United States Patent [19]

Frulla et al.

[11] Patent Number: 4,567,287

[45] Date of Patent: Jan. 28, 1986

[54] PREPARATION OF CARBAMATES FROM ORGANIC CARBONATES AND AROMATIC UREAS

[75] Inventors: Floro F. Frulla, Wallingford; Fred A. Stuber, North Haven; Peter J. Whitman, Hamden, all of Conn.

[73] Assignee: The Upjohn Co., Midland, Mich.

[21] Appl. No.: 638,800

[22] Filed: Aug. 8, 1984

[51] Int. Cl.$^4$ ............... C07C 125/065; C07C 125/073
[52] U.S. Cl. ...................................... 560/024; 560/25
[58] Field of Search ..................................... 560/24, 25

[56] References Cited

U.S. PATENT DOCUMENTS

| | | | |
|---|---|---|---|
| 3,627,813 | 12/1971 | Abbate et al. | 260/471 C |
| 3,763,217 | 10/1973 | Brill | 560/24 |
| 4,100,351 | 7/1978 | Romano et al. | 560/24 |
| 4,381,404 | 4/1983 | Buysch et al. | 560/24 |

Primary Examiner—Bernard Helfin
Attorney, Agent, or Firm—James S. Rose

[57] ABSTRACT

Disclosed is an improved process for the preparation of carbamates by heating an organic carbonate and an aromatic urea or polyurea in the presence of aluminum as catalyst and a promoter comprising a combination of iodine and a mercury salt.

High reaction temperatures are avoided by the process and conversions to carbamate products are high. Additionally, the process is economically attractive because even the common aluminum foil can be used as the catalyst.

The products prepared by the process can be used in the production of insecticides, and, particularly, as intermediates in the preparation of organic mono- and polyisocyanates.

18 Claims, No Drawings

PREPARATION OF CARBAMATES FROM ORGANIC CARBONATES AND AROMATIC UREAS

BACKGROUND OF THE INVENTION

1. Field of the Invention

This invention relates to carbamates and is more particularly concerned with an improved process for the preparation of carbamates from aromatic substituted ureas and organic carbonates.

2. Description of the Prior Art

The preparation of alkyl N-hydrocarbylcarbamates from N-hydrocarbyl substituted ureas and dialkyl carbonates using various types of basic catalysts has been disclosed in U.S. Pat. No. 3,627,813. The catalysts included alkali metal hydroxides, alkali metal alkoxides, and tertiary organic amines. When using the above method with ureas having other base sensitive chemical linkages, the strong basic catalysts can have a deleterious effect on the yield of desired carbamates.

U.S. Pat. No. 4,381,404 discloses a similar method to that disclosed in the patent cited supra. However, the catalysts employed are inorganic or organic compounds of aluminum, lead, magnesium, titanium, tin, zinc, or zirconium. While this reference avoids the strong bases of the prior patent, generally speaking, relatively high reaction temperatures are required in order to isolate the carbamate products in good yield.

It has now been found that aluminum metal in combination with traces of a promoter combination will catalyze the reaction of N-aromatic substituted ureas with organic carbonates to form the corresponding carbamates in high conversions.

Compared with the prior art methods, the process in accordance with the present invention provides an improvement because it avoids the use of strong basic catalysts and the need for high reaction temperatures.

Further, low cost aluminum in any form can be employed along with only trace amounts of the promoter combination. Accordingly, the present method provides additional economic benefits compared to prior art methods.

SUMMARY OF THE INVENTION

This invention comprises an improved process for the preparation of carbamates by reacting an organic carbonate with a urea selected from the group consisting of an aromatic urea, an aromatic polyurea, and mixtures thereof in the presence of a catalyst, wherein the improvement comprises employing aluminum as catalyst with a promoter comprising a combination of a mercury salt and iodine.

The term "aromatic urea" means a compound having the formula $$RNHCONHR^1 \qquad\qquad I$$

wherein R is an aromatic radical defined below and $R^1$ is selected from the group consisting of hydrogen, alkyl, aralkyl, cycloalkyl, and the aromatic radical R.

The term "aromatic polyurea" means a compound having the formula $$RNHCO-NHR^2NHCO)_m NHR^1 \qquad\qquad II$$

wherein R and $R^1$ have the same significance set forth above, $R^2$ is a divalent aromatic radical defined below and m has a value of at least 1.

The term "aromatic radical" means the radical obtained by removing one nuclear hydrogen atom from an aromatic compound having from 6 to 36 carbon atoms and is inclusive of radicals having the formulae

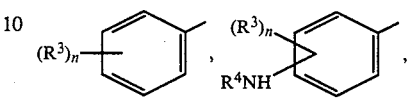

III    IV

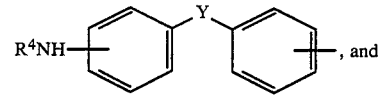

V

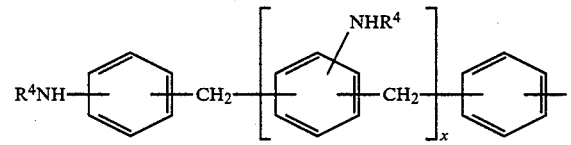

VI wherein $R^3$ is selected from the group consisting of hydrocarbyl and inert substituents, n is 0 to 2, $R^4$ is selected from the group consisting of hydrogen, and —$COOR^5$, wherein $R^5$ represents a monovalent organic radical (preferably $C_1$ to $C_4$ alkyl or phenyl), Y is selected from the group consisting of —O—, —CO—, —$SO_2$—, and a single bond, and x is an integer from 0 to 6 or in the case of a mixture x has a mean value greater than 0 but less than 1.

The term "hydrocarbyl" means the radical obtained by removing one hydrogen atom from the parent hydrocarbon having from 1 to 8 carbon atoms. Illustrative of hydrocarbyl are alkyl such as methyl, ethyl, propyl, butyl, pentyl, hexyl, octyl, and the like, including isomeric forms thereof; alkenyl such as vinyl, allyl, butenyl, pentenyl, hexenyl, octenyl, and the like, including isomeric forms thereof; aralkyl such as benzyl, phenethyl, and the like; aryl such as phenyl, tolyl, xylyl, and the like; cycloalkyl such as cyclobutyl, cyclopentyl, cyclohexyl, cycloheptyl, cyclooctyl, and the like, including isomeric forms thereof; and cycloalkenyl such as cyclopentenyl, cyclohexenyl, cycloheptenyl, cyclooctenyl, and the like, including isomeric forms thereof.

The term "inert substituent" means any radical other than hydrocarbyl defined above which does not react with the urea groups or otherwise interfere with the process in accordance with the present invention. Illustrative of such substituents are halo, i.e. chloro, bromo, fluoro, iodo; nitro; alkoxy from 1 to 8 carbon atoms, inclusive, such as methoxy, ethoxy, propoxy, butoxy, pentyloxy, hexyloxy, heptyloxy, octyloxy, and the like, including isomeric forms thereof; alkylmercapto from 1 to 8 carbon atoms, inclusive, such as methylmercapto, ethylmercapto, propylmercapto, butylmercapto, pentylmercapto, hexylmercapto, heptylmercapto, octylmercapto, and the like, including isomeric forms thereof; and cyano.

The terms "alkyl", "aralkyl", and "cycloalkyl" in respect of the radical $R^1$ have the same definitions set forth above in the hydrocarbyl group.

The term "divalent aromatic radical" means the radical obtained by removing a second nuclear hydrogen atom from the aromatic radicals defined in the above formulae with the exceptions that no $R^4NH-$ radicals are present in the formulae, the divalent radicals from III and IV become identical, the value of x in VI is limited to 0.

DETAILED DESCRIPTION OF THE INVENTION

The improved process in accordance with the present invention can be carried out using any of the aromatic ureas and organic carbonates along with the general reaction procedures and techniques disclosed in U.S. Pat. Nos. 3,627,813 and 4,381,404 cited supra whose disclosures relative thereto are incorporated herein by reference. The novel feature of the present process which will be discussed in detail below resides in the use of aluminum metal as a catalyst along with the promoter combination comprising the mercury salt and iodine.

The following equation shows, by way of illustration only, the formation of the carbamate products from the reaction of the aromatic urea having the formula I with dimethyl carbonate:

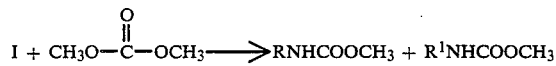

As will be readily understood by one skilled in the art, when the radical $R^1$ in I is an aromatic radical and has the same identity as the other radical R, then the two molecules of carbamate product are identical.

ent carbamates in accordance with the present invention, it will be readily understood that under certain circumstances all three of the carbamates can be identical. For example, when R and $R^1$ are identical aromatic radicals having themselves substituent radicals $R^4NH-$ wherein $R^4$ is a $-COOCH_3$ group and $R^2$ is the divalent radical related to R and $R^1$ as described above, then the product of the reaction would be m+2 moles of the identical carbamate.

Accordingly, mixtures in any proportions comprising polyureas of formula II, or mixtures of monourea I and polyurea II wherein R and $R^1$ are common aromatic radicals and $R^2$ is the related divalent radical as defined above can be converted in accordance with the present process to a single pure carbamate product. Mixtures of monoureas and polyureas similar to those mixtures referred to above are obtained as by-products during the preparation of carbamates by the reaction of aromatic amines with organic carbonates as disclosed in copending application Ser. No. 625,060 filed June 27, 1984. The present process can be employed to convert these by-products to the carbamates thereby increasing product yields accordingly.

Any of the N-aryl, N,N'-diaryl substituted ureas and aromatic polyureas disclosed in the patents cited supra and already incorporated herein by reference can be employed in the present process including methods for their preparation.

Illustrative, but not limiting of ureas which can be employed are N-phenylurea, N-(m-tolyl)urea, N-(p-tolyl)urea, N-phenyl-N'-methylurea, N-phenyl-N'-ethylurea, N-phenyl-N'-butylurea, N-phenyl-N'-hexylurea, N-phenyl-N'-benzylurea, N-phenyl-N'-phenethylurea, N-phenyl-N-cyclohexylurea, N,N'-diphenylurea, N,N'-di(m-tolyl)urea, N,N'-di(p-tolyl)urea, and ureas having the following formulae

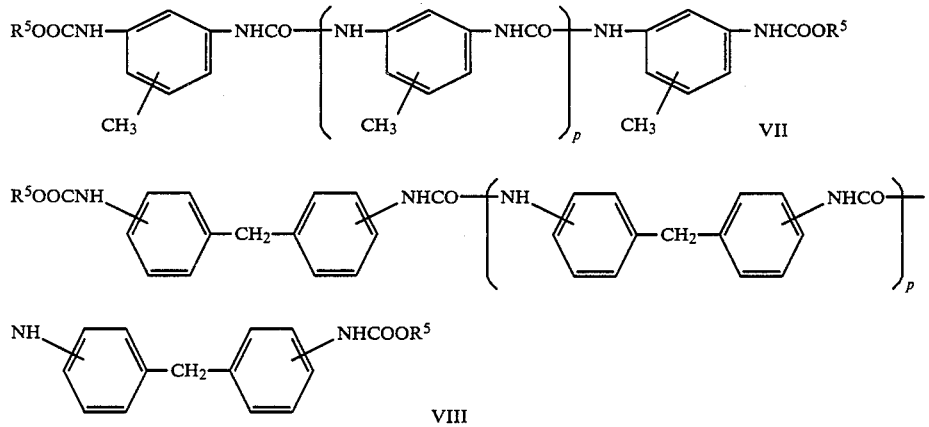

Where R and $R^1$ are different, the product of the process will be a mixture of the two different carbamates.

Similarly, the process of the invention as applied to aromatic polyureas can be schematically represented by the following equation:

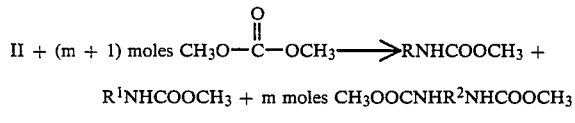

wherein R, $R^1$ and $R^2$ are defined as above. Although the above equation shows the formation of three differwherein $R^5$ is preferably alkyl such as methyl, ethyl, butyl and the like, p is an integer from 0 to 4, or in the case of a mixture p has a mean value greater than 0 but less than 1. In the case of polyureas the molecular weights can vary considerably but generally speaking do not exceed about 4000.

A preferred group of ureas consists of those wherein R and $R^1$ are both aromatic radicals such as N,N'-diphenylurea, N,N'-di(m-tolyl)urea, N,N'-di(p-tolyl)urea, and the ureas having the formulae VII and VIII.

The carbonates can be any of the organic esters of carbonic acid disclosed in the art cited supra including the dialkyl, diaryl, diaralkyl, and cyclic esters which, illustratively includes dimethyl carbonate, diethyl carbonate, dipropyl carbonate, dibutyl carbonate, diamyl carbonate, dihexyl carbonate, methyl ethyl carbonate, diphenyl carbonate, dibenzyl carbonate, ethylene carbonate, propylene carbonate, and the like.

A preferred group comprises the dialkyl carbonates such as dimethyl carbonate, diethyl carbonate, dipropyl carbonate, and dibutyl carbonate.

The proportions in which the carbonate and the urea are employed are in no way critical to the process in accordance with the invention. Obviously, to obtain complete conversion of urea to carbamate the carbonate must be present in at least a molar equivalency for each equivalent of urea present (molecular weight of aromatic urea divided by the number of urea groups).

Generally speaking, it is preferred that the carbonate be employed in excess over the urea to minimize side reactions and to serve as a solvent for the reaction. Advantageously, the carbonate is employed in at least a 5 molar excess in respect of each equivalent of urea, and, preferably, in a range of from about 5 to about 30 moles of carbonate per equivalent of urea.

The aluminum catalyst can be used as either the pure metal or as an alloy thereof. If an alloy be employed, the aluminum should be the major constituent thereof, i.e. at least 50 percent by weight. Typical of such alloys are aluminum/copper/silicon (87.5%/3.5%/9.0% by weight), aluminum/magnesium (90%/10% by weight), and the like. The pure metal is preferred.

The form in which the aluminum is employed is in no way critical and can be a finely divided powder or as pieces of aluminum rods, sheets, scrap, strips of aluminum foil, and the like.

The optimum quantity of aluminum to be used in any given reaction will vary somewhat depending on the reactants and conditions but can be readily determined by one skilled in the art. Advantageously, the aluminum is employed in an amount of from about 0.1 mole to about 2 moles per equivalent of urea groups, and, preferably, from about 0.2 to about 1.0 mole per equivalent of urea.

The promoter in accordance with the present process comprises the combination of iodine and a mercury salt. The term "mercury salt" means a mercurous or mercuric salt inclusive of inorganic and organic salts such as mercurous chloride, mercurous fluoride, mercurous bromide, mercurous nitrate, mercurous sulfate, mercurous acetate, mercuric chloride, mercuric iodide, mercuric bromide, mercuric fluoride, mercuric sulfate, mercuric nitrate, mercuric acetate, mercuric basic carbonate, and the like.

The preferred mercury salts are in the mercuric state.

A preferred promoter combination comprises mercuric chloride and iodine.

As is usually the case with catalyzed reactions involving a promoter, the role of the promoter mixture is not well understood. Generally speaking, just trace amounts of the promoters will give rise to the improved process in accordance with the present invention. Advantageously, the iodine and mercuric salt are each employed in an amount falling within the proportions of about 0.001 part by weight to 1 part by weight per equivalent of urea, preferably, about 0.01 to 0.5 part by weight per equivalent of urea.

One of the particular advantages of the present process is the fact that it is carried out under atmospheric pressure and relatively low reaction temperatures. This is not to say that the process cannot be conducted under pressure conditions if one so chooses. However, there is no particular need to do so as very high conversions to desired carbamates are achieved at normal atmospheric conditions which is, in turn, related to the relatively low temperature conditions employed. In this connection, the reaction is generally conducted at a temperature of from about 75° C. to about 200° C., preferably from about 100° C. to about 150° C., most preferably from about 100° C. to about 140° C.

The reactants along with the catalyst and promoter combination can be mixed in any order and heated to a reaction temperature falling within the above range until the reaction is judged to be complete. The completion of the reaction is easily determined using known standard analytical procedures to assay the disappearance of the reactants or maximum appearance of carbamate. Typical methods are infrared absorption analysis, gel permeation chromatography, high pressure liquid chromatography, and the like.

The carbamates are isolated from the reaction mixture using standard separation procedures. Typically, the reaction solution is mixed with water and the carbamate is extracted from the aqueous solution using a water insoluble organic solvent, for example a halogenated solvent such as chloroform, carbon tetrachloride, methylene dichloride, and the like. The organic solution is separated from the aqueous phase and the solvent removed using standard methods to provide the residual carbamate. The carbamate, if desired, can be purified using standard methods such as recrystallization, column chromatography, and the like.

As pointed out previously, the process of the invention can be applied to the conversion of monoureas, polyureas, or mixtures thereof to carbamate products. In a particular aspect of the invention, the process described above can be applied to molecules which contain a plurality of urea linkages in a polymeric chain. For example, the process of the invention can be applied to the treatment of polyureas and polyurethane/polyureas such as are obtained by reaction of a polyisocyanate and a polyamine or reaction of an isocyanate-terminated polyurethane prepolymer with a polyamine. The use of the process of the invention in this manner enables one to modify the properties of a polyurea or polyurethane/urea by shortening the chain length of said polymer and by introducing carbamate groups as terminal groups in the polymer chain. The latter groups can obviously be converted, as by acid hydrolysis of the ester and decarboxylation of the free carbamic acid, to the corresponding primary amino group thereby giving rise to an active center for further modification of the polymer.

The extent to which a polyurea or polyurethane/urea can be modified in the above manner is controlled by varying the amount of dialkyl carbonate employed in the reaction as well as by varying time and temperature. If desired, complete degradation of the polyurea or polyurethane/polyurea can be achieved, i.e. all the urea linkages in the polymer chain can be subjected to conversion. Thus the process of the invention can be employed to recover scrap polyurea, or scrap polymer containing urea linkages, by converting the scrap to carbamate corresponding to the polyamine from which the polymer was originally prepared.

The carbamate products produced in accordance with the present process are used in a number of applications including the production of pesticides, and, particularly, as intermediates for the preparation of organic isocyanates by thermal cracking into the isocyanate and alcohol component using known methods.

The following examples describe the manner and process of making and using the invention and set forth the best mode contemplated by the inventors of carrying out the invention but are not to be construed as limiting.

EXAMPLE 1

The following experiment describes the preparation of ethyl-N-phenylcarbamate in accordance with the present invention.

A 250 ml. three-neck reaction flask was equipped with a mechanical stirrer, thermometer, reflux condenser, and a nitrogen inlet tube. The flask was charged with 1.0 g. (0.0047 equiv.) of N,N'-diphenylurea, 14.0 g. (0.119 mole) of diethyl carbonate, 0.1 g. (0.0037 mole) of aluminum foil (Alcoa Wrap) cut into small strips, a very small quantity of iodine (estimated about 0.001 g.), and about the same quantity (0.001 g.) of mercuric chloride.

Under a steady nitrogen purge and during stirring the reaction mixture was heated in an oil bath controlled to 134° to 135° C. The heating and stirring was continued for a total period of about 17.5 hours.

The reaction solution was mixed with 50 ml. of water and the mixture extracted with 2×25 ml. portions of methylene dichloride. The separated aqueous phase contained a gelatinous precipitate which was collected by suction filtration which precipitate was washed with methylene chloride. The washings were combined with the main methylene chloride solution. The combined organic phases were dried by storage over sodium sulfate and then the solvent stripped using a rotary evaporator under about 10 mm. of mercury pressure and a heating bath at about 60°–70° C. The residue was 2.16 g. of a light amber colored liquid.

A sample of the residue was analyzed by high pressure liquid chromatography (hplc) employing a 3.9 mm×30 cm $\mu C_{18}$ column using acetonitrile/water (isocratic, 45/55 v/v) at a flow rate of 1.5 cc/minute and pressure about 118 atm. By the use of internal standards, the yields of the products obtained from the reaction were determined as follows: aniline=1.0%, ethyl-N-phenylcarbamate=98.2%, N,N'-diphenylurea=0.4%, and N-ethylaniline=0.3%.

EXAMPLE 2

The following experiment describes the preparation of 4,4'-methylenebis(N-carbethoxyaniline) in accordance with the present invention.

A 250 ml. Erlenmeyer flask fitted with a magnetic stirrer was charged with 90 g. of absolute ethanol and 10 g. (0.56 mole) of water. To the aqueous-alcohol solution was added portionwise 10.0 g. (0.04 mole) of 4,4'-methylenebis(phenyl isocyanate). The stirred mixture was heated at about 50° C. for approximately 1 hour. A white precipitate formed during the heating period. An excess of chloroform was added to the cooled reaction mixture and stirring continued for a prolonged period (about 24 hours). The precipitate was collected by filtration, washed with 3×150 ml. portions of chloroform, and dried at 60° to 70° C. under a vacuum of about 1.0 mm. of mercury pressure to provide 2.91 g. of a white polyurea related to formula (VIII) and having the formula

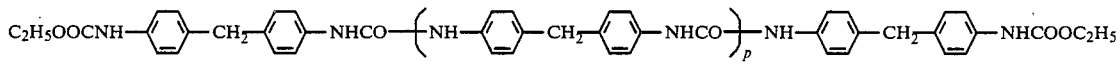

An infrared spectrum (KBr pellet) of the polyurea was identical to the spectrum for a known polyurea having the above formula. Proton nuclear magnetic resonance (NMR) of the product disclosed a ratio of diaryl methylene protons to methylene protons of the carbethoxy group of 2.6. Therefore, the value of p is about 3.2.

A 50 ml. reaction flask was equipped with a magnetic stirrer, a reflux condenser, thermometer, and a nitrogen inlet tube. The flask was charged with 2.0 g. (0.007 equiv.) of the polyurea prepared above, 14.0 g. (0.118 mole) of diethyl carbonate, and 0.1 g. (0.004 mole) of aluminum foil (Kaiser Wrap) cut into small pieces. The mixture was heated using an oil bath set to cycle at about 140° C. and when the temperature of the reactants had reached about 120° C. about 0.001 g. each of iodine and mercuric chloride were added. Under a slow stream of nitrogen and with gentle reflux, the solution was heated at about 140° C. for about 16 hours.

The cooled reaction solution was mixed with 50 ml. of water followed by the addition of 150 ml. of chloroform. Some solids precipitated which were separated by filtration. The liquid phase was separated and extracted with 2×50 ml. portions of chloroform. The organic phases were combined and dried by storage over sodium sulfate. The sodium sulfate was removed by filtration and the chloroform removed by heating the solution at 60° to 70° C. first under water aspirator pressure (about 10 mm. of mercury pressure) followed by vacuum pump pressure (about 0.1 mm mercury pressure). A residue of 2.80 g of light brown waxy material remained.

An infrared spectrum in chloroform of this residue was in good agreement with the infrared spectrum of a crude sample of authentic 4,4'-methylenebis(N-carbethoxyaniline) prepared by a different process.

A gel permeation chromatography assay of the above residue disclosed higher molecular weight components of 7.8 and 9.4 weight percent and the 4,4'-methylenebis(N-carbethoxyaniline) product at 82.8 weight percent which latter is equivalent to an 85 mole percent yield of desired product.

We claim:

1. In a process for the preparation of a carbamate by heating at a temperature of from about 75° C. to about 200° C. at least a molar equivalency of an organic carbonate selected from the group consisting of dialkyl, diaryl, diaralkyl, and cyclic esters of carbonic acid with each equivalent of a urea selected from the group consisting of an aromatic urea, an aromatic polyurea, and mixtures thereof in the presence of a catalyst, the improvement which comprises employing aluminum metal as catalyst with a promoter combination of a mercury salt and iodine.

2. A process according to claim 1 wherein the reaction temperature is from about 100° C. to about 150° C.

3. A process according to claim 1 wherein said aluminum catalyst is employed in an amount of from about 0.1 mole to about 2 moles per equivalent of urea groups present.

4. A process according to claim 1 wherein said mercury salt and said iodine are each employed in an amount falling within the proportions by weight of about 0.001 part to 1 part per equivalent of urea groups present.

5. A process according to claim 1 wherein said organic carbonate is employed in at least a 5 molar excess in respect of each equivalent of urea groups present.

6. A process according to claim 1 wherein said organic carbonate is a dialkyl carbonate.

7. A process according to claim 6 wherein said carbonate is diethyl carbonate.

8. A process according to claim 1 wherein said mercury salt is in the mercuric state.

9. A process according to claim 8 wherein said salt is mercuric chloride.

10. A process according to claim 1 wherein said urea is an aromatic urea.

11. A process according to claim 1 wherein said urea is an aromatic polyurea.

12. A process for preparing a carbamate from a dialkyl carbonate and a urea, said process comprising heating at a temperature of about 100° C. to about 150° C. a mixture comprising at least a molar equivalency of said dialkyl carbonate with each equivalent of a urea selected from the group consisting of an aromatic urea, aromatic polyurea, and mixtures thereof in the presence of an aluminum metal catalyst and a promoter comprising a combination of a mercuric salt and iodine.

13. A process according to claim 12 wherein said aluminum catalyst is employed in an amount of from about 0.1 mole to about 2 moles per equivalent of urea groups present.

14. A process according to claim 12 wherein said mercuric salt and iodine are each employed in an amount falling within the proportions by weight of about 0.001 part to 1 parts per equivalent of urea groups present.

15. A process according to claim 12 wherein said mercuric salt is mercuric chloride.

16. A process according to claim 12 wherein said dialkyl carbonate is diethyl carbonate.

17. A process according to claim 12 wherein diethyl carbonate and N,N-diphenylurea are converted to ethyl N-phenylcarbamate.

18. A process according to claim 12 wherein diethyl carbonate and the polyurea obtained from the reaction of methylenebis(phenyl isocyanate) with aqueous-ethanol are converted to methylenebis(N-carbethoxyaniline).

* * * * *

UNITED STATES PATENT AND TRADEMARK OFFICE
CERTIFICATE OF CORRECTION

PATENT NO. : 4,567,287

DATED : January 28, 1986

INVENTOR(S) : Floro F. Frulla, Fred A. Stuber, and Peter J. Whitman

It is certified that error appears in the above-identified patent and that said Letters Patent is hereby corrected as shown below:

Title page:

Under the Assignee section [73] "The Upjohn Company" should read -- The Dow Chemical Company --.

Signed and Sealed this

Tenth Day of March, 1987

Attest:

DONALD J. QUIGG

Attesting Officer

Commissioner of Patents and Trademarks